US008867703B2

(12) United States Patent
Shapiro et al.

(10) Patent No.: US 8,867,703 B2
(45) Date of Patent: *Oct. 21, 2014

(54) MULTI-MODE CONE BEAM CT RADIOTHERAPY SIMULATOR AND TREATMENT MACHINE WITH A FLAT PANEL IMAGER

(75) Inventors: Edward G. Shapiro, Menlo Park, CA (US); Edward J. Seppi, Portola Valley, CA (US); John M. Pavkovich, Palo Alto, CA (US); Peter Munro, Mountain View, CA (US); Stanley W. Johnsen, Palo Alto, CA (US); Richard E. Colbeth, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 13/352,222

(22) Filed: Jan. 17, 2012

(65) Prior Publication Data

US 2012/0114094 A1     May 10, 2012

Related U.S. Application Data

(63) Continuation of application No. 11/891,505, filed on Aug. 10, 2007, now Pat. No. 8,116,430, which is a continuation of application No. 10/324,227, filed on Dec. 18, 2002, now Pat. No. 7,945,021.

(51) Int. Cl.
    *A61N 5/10*     (2006.01)
    *A61B 6/00*     (2006.01)
    *A61B 6/03*     (2006.01)

(52) U.S. Cl.
    CPC .............. *A61B 6/4233* (2013.01); *A61B 6/032* (2013.01); *A61N 5/1049* (2013.01); *A61N 2005/1054* (2013.01); *A61B 6/4085* (2013.01)

USPC .............................................. 378/65; 378/20

(58) Field of Classification Search
    CPC ........ A61B 6/032; A61B 6/4085; A61N 5/10; A61N 5/103; A61N 5/1042; A61N 5/1048; A61N 5/1049; A61N 2005/1054; A61N 2005/1061
    USPC ....................................................... 378/65, 20
    See application file for complete search history.

(56) References Cited

U.S. PATENT DOCUMENTS 3,133,227 A    5/1964   Brown et al.
3,144,552 A    8/1964   Schonberg (Continued)

FOREIGN PATENT DOCUMENTS

DE    4223488      1/1994
DE    19614643     10/1997

(Continued)

OTHER PUBLICATIONS

"Advanced Workstation for Irregular Field Simulation and Image Matching", *Copyright MDS Nordion*, (1999), 7 pages.

(Continued)

*Primary Examiner* — Allen C. Ho
(74) *Attorney, Agent, or Firm* — Blakely, Sokoloff, Taylor & Zafman, LLP

(57) ABSTRACT

A multi-mode cone beam computed tomography radiotherapy simulator and treatment machine is disclosed. The radiotherapy simulator and treatment machine both include a rotatable gantry on which is positioned a cone-beam radiation source and a flat panel imager. The flat panel imager captures x-ray image data to generate cone-beam CT volumetric images used to generate a therapy patient position setup and a treatment plan.

21 Claims, 4 Drawing Sheets

Simulator kV Cone Beam CT Diagram

(56) References Cited

U.S. PATENT DOCUMENTS

| | | | |
|---|---|---|---|
| 3,193,717 | A | 7/1965 | Nunan |
| 4,149,247 | A | 4/1979 | Pavkovich et al. |
| 4,149,248 | A | 4/1979 | Pavkovich |
| 4,208,675 | A | 6/1980 | Bajon et al. |
| 4,209,706 | A | 6/1980 | Nunan |
| 4,521,808 | A | 6/1985 | Ong et al. |
| 4,593,967 | A | 6/1986 | Haugen |
| 4,675,731 | A | 6/1987 | Takasu et al. |
| 4,679,076 | A | 7/1987 | Vikterlof et al. |
| 4,726,046 | A | 2/1988 | Nunan |
| 4,741,621 | A | 5/1988 | Taft et al. |
| 4,825,393 | A | 4/1989 | Nishiya |
| 4,853,777 | A | 8/1989 | Hupp |
| 4,868,844 | A | 9/1989 | Nunan |
| 5,014,292 | A | 5/1991 | Siczek et al. |
| 5,027,818 | A | 7/1991 | Bova et al. |
| 5,039,867 | A | 8/1991 | Nishihara et al. |
| 5,080,100 | A | 1/1992 | Trotel |
| 5,099,505 | A | 3/1992 | Seppi et al. |
| 5,117,445 | A | 5/1992 | Seppi et al. |
| 5,168,532 | A | 12/1992 | Seppi et al. |
| 5,247,555 | A | 9/1993 | Moore et al. |
| 5,262,649 | A | 11/1993 | Antonuk et al. |
| 5,335,255 | A | 8/1994 | Seppi et al. |
| 5,394,452 | A | 2/1995 | Swerdloff et al. |
| 5,400,255 | A * | 3/1995 | Hu .................................. 378/4 |
| 5,438,991 | A | 8/1995 | Yu et al. |
| 5,471,516 | A | 11/1995 | Nunan |
| 5,537,452 | A | 7/1996 | Sheopard et al. |
| 5,661,773 | A | 8/1997 | Swerdloff et al. |
| 5,692,507 | A | 12/1997 | Seppi et al. |
| 5,751,781 | A | 5/1998 | Brown et al. |
| 5,926,521 | A * | 7/1999 | Tam .................................. 378/4 |
| 5,949,811 | A | 9/1999 | Baba et al. |
| 5,956,382 | A | 9/1999 | Wiener-Avnear et al. |
| 5,960,055 | A * | 9/1999 | Samarasekera et al. ........... 378/4 |
| 5,999,587 | A | 12/1999 | Ning et al. |
| 6,031,888 | A | 2/2000 | Ivan et al. |
| 6,041,097 | A | 3/2000 | Roos et al. |
| 6,075,836 | A * | 6/2000 | Ning ........................ 378/98.12 |
| 6,078,638 | A * | 6/2000 | Sauer et al. ........................ 378/4 |
| 6,104,778 | A | 8/2000 | Murad |
| 6,104,780 | A | 8/2000 | Hanover et al. |
| 6,144,875 | A | 11/2000 | Schweikard et al. |
| 6,219,403 | B1 | 4/2001 | Mishihara |
| 6,219,441 | B1 * | 4/2001 | Hu ................................ 382/131 |
| 6,222,901 | B1 | 4/2001 | Meulenbrugge et al. |
| 6,269,141 | B1 * | 7/2001 | Proksa et al. ..................... 378/19 |
| 6,292,526 | B1 | 9/2001 | Patch |
| 6,307,914 | B1 | 10/2001 | Kunieda et al. |
| 6,325,537 | B1 | 12/2001 | Watanabe |
| 6,325,758 | B1 | 12/2001 | Carol et al. |
| 6,370,421 | B1 | 4/2002 | Williams et al. |
| 6,381,302 | B1 | 4/2002 | Berestov |
| 6,385,286 | B1 | 5/2002 | Fitchard et al. |
| 6,385,288 | B1 | 5/2002 | Kanematsu |
| 6,429,578 | B1 | 8/2002 | Danielsson et al. |
| 6,463,122 | B1 | 10/2002 | Moore |
| 6,480,565 | B1 | 11/2002 | Ning |
| 6,504,892 | B1 * | 1/2003 | Ning .................................. 378/4 |
| 6,508,586 | B2 | 1/2003 | Oota |
| 6,590,953 | B2 | 7/2003 | Suzuki et al. |
| 6,661,870 | B2 | 12/2003 | Kapatoes et al. |
| 6,744,848 | B2 | 6/2004 | Stanton et al. |
| 6,842,502 | B2 | 1/2005 | Jaffray et al. |
| 6,865,254 | B2 | 3/2005 | Nafstadius |
| 6,888,919 | B2 | 5/2005 | Graf |
| 6,914,959 | B2 | 7/2005 | Baily et al. |
| 7,945,021 | B2 * | 5/2011 | Shapiro et al. .................. 378/65 |
| 8,116,430 | B1 * | 2/2012 | Shapiro et al. .................. 378/65 |
| 2001/0001807 | A1 | 5/2001 | Green |
| 2001/0008271 | A1 | 7/2001 | Ikeda et al. |
| 2002/0066860 | A1 | 6/2002 | Possin |
| 2003/0007601 | A1 | 1/2003 | Jaffray et al. |

FOREIGN PATENT DOCUMENTS

| | | |
|---|---|---|
| EP | 0062941 | 9/1984 |
| EP | 0205720 | 12/1986 |
| EP | 0480035 | 11/1994 |
| EP | 0948930 | 10/1999 |
| FR | 2269745 | 11/1975 |
| FR | 2551664 | 3/1985 |
| GB | 1328033 | 8/1973 |
| JP | 5057028 | 3/1993 |
| JP | 63294839 | 12/1998 |
| WO | WO-8503212 | 8/1985 |
| WO | WO-9014129 | 11/1990 |
| WO | WO-9200567 | 1/1992 |
| WO | WO-9220202 | 11/1992 |
| WO | WO-01/60236 | 2/2001 |
| WO | WO-0160236 | 8/2001 |
| WO | WO-02/13907 | 2/2002 |
| WO | WO-0213907 | 2/2002 |

OTHER PUBLICATIONS

Andrew, et al., "A video-Based Patient Contou Acquisition System for the Design Radiotherapy Compensators", Abstract, *Med Phys*, vol. 16 (3), (May-Jun. 1989), 425-430.

Balter, J M., et al., "Daily Targeting of intrahepatic tumors for Radiotherapy", *Int. J. Radiation Oncology Biol. Phys.*, vol. 52, No. 1, (2002), 166-271.

Brewsterfuauf, et al., "Automatic Generation of Beam Apertures", Abstract, *Medical Physics*, vol. 20, (1993), 1337, 1342.

Cho, P S., et al., "Cone-Beam CT for Radiotherapy Applications", *Phys. Med. Biol*, vol. 40, (1995), 1863-1883.

Drake, D G., et al., "Characterization of a Fluoroscopic Imaging System for kV and MV Radiography", *Med. Phys.*, vol. 27, No. 5, (May 2000), 898-905.

Elliot, et al., "Interactive Imagine Segmentation for Radiation Treatment Planning", Abstract, *IBM Systems Journal*, vol. 31, No. 4, (1992), 620-634.

Fahrig, R , et al., "Three-Dimensional Computed Tomographic Reconstruction Using a C-Arm Mounted XRII: Image Based Correction of Gantry Motion Nonidealities", *Med. Phys.*, vol. 27, No. 1, (Jan. 2000), 30-38.

Feldkamp, L A., et al., "Practical Cone-Beam Algorithm", *J. Opt. Soc. Am. A*, vol. 1, No. 6, (Jun. 1984), 612-619.

Gademann, et al., "Three-Dimensional Radiation Planning. Studies on Clinical Integration", Abstract, *Strahlenther Onkol*, vol. 169 (3), (1993), 159-167.

Groh, B A., et al., "A Performance Comparison of Flat-Panel Imager-Based MV and kV Conebeam CT", *Med. Phys.*, vol. 29, No. 6, (Jun. 2002), 967-975.

Hara, et al., "Radiotherapeutic System", 00480035/EP-B1, Citation from World Patent, (1994), 1 page.

Jaffray, et al., *SPIE*, vol. 3659, (1999), 204-214.

Jaffray, D A., et al., "A Radiographic and Tomographic Imaging System Integrated into a Medical Linear Accelerator for Localization of Bone and Soft-Tissue Targets", *Int. J. Radiation Oncology Biol. Phys.*, vol. 45, No. 3, (1999), 779-789.

Jaffray, D A., et al., "Cone-Beam Computed Tomography with a Flat-Panel Imager: Initial Performance Characterization", *Med. Phys.*, Col. 27, No. 6, (Jun. 2000), 1311-1323.

Jaffray, et al., "Cone-Beam CT: Applications in Image-Guided External Beam Radiotherapy and Brachytherapy", *Engineering in medicine and Biology Society, Proceedings of the 22nd Annual International conference of the IEEE*, vol. 3, (Jul. 2000), 2044.

Jaffray, et al., "Flat-Paneled Cone-Beam Computed Tomography for Image-Guided Radiation Therapy", *Int. J. Radiation Oncology Biol. Phys.*, vol. 53, No. 5, (2002), 1337-1349.

Keys, D , et al., "A CCTV-Microcomputer Biostereometric System for Use in Radiation Therapy (Topography, Medical Physics, Tissue Compensators)", Abstract, *Energy Science and Technology*, vol. 45-12B, (1984), 3857.

Kudo, et al., "Feasible Cone Beam Scanning Methods for Exact Reconstruction in Three-Dimensional Tomography", *J. Opt. Soc. Am. A.*, 7, (1990), 2169.

(56) References Cited

OTHER PUBLICATIONS

Kuhn, MH , "AIM Project A2003: Computer Vision in Radiology (COVIRA)", Abstract, *Computer Methods and Programs in Biomedicine*, vol. 45, No. 1-2, (Oct. 1994), 17-31.

Kushima, GJ , et al., "New Development of Integrated CT Simulation System for Radiation Therapy Planning", Abstract. *Kobe J. Med. Sci.*, vol. 9, No. 5-6, (Dec. 1993), 17-213.

Kutcher, et al., "Three Dimensional Radiation Treatment Planning", Abstract (1998), *Dosimetry in Radiotherapy* vol. 2, *Proceedings of an international symposium* Held in Vienna, Austria, (Aug.-Sep. 1987).

Masahiro, et al., "Patient Beam Positioning System Using CT Images", *Phys. Med. Biol.*, vol. 27, No. 2, (1982), 301-305.

Midgley, et al., "A Feasibility Study for Megavoltage Cone Beam CT Using a Commercial EPID", *Phys. Med. Biol. 43*, United Kingdom, (1998), 155-169.

Mohan, et al., "Intersection of Shaped Radiation Beams with Arbitrary Image Sections", Abstract, *Comput Methods Programs Biomed*, vol. 24, (Jun. 1987), 161-168.

Mosleh-Shirazi, M A., et al., "A Cone-Beam Megavoltage CT Scanner for Treatment Certification in Conformal Radiotherapy", *Radiotherapy and Oncology*, vol. 48, (1998), 319-328.

Nakagawa, K , et al., "Megavoltage CT-Assisted Stereotactic Radiosurgery for Thoracic Tumors: Original Research in the Treatment of Thoracic Neoplasms", *Int. J. radiation ongology biol. phys.*, col. 48, No. 2, (2000), 449-457.

Ning, et al., *SPIE*, vol. 3659, (1999), 192-203.

Ning, et al., "Flat Panel Detector-Based Cone-Beam Volume CT Anglography Imagrng System Evaluation", *EEE Transactions on Medical Irnaglng*, vol. 19, No. 9, Sep. 2000, 949-963.

Ning, et al., "Image Intensifier-Based Volume Tomographic Angiography Imaging System: System Evaluation", *SPIE*, vol. 2432, (Medical Imaging 1995), 280-290.

Pisani, L , et al., "Setup Error in radiotherapy: On-line Correction using Electronic Kilovoltage and Megavoltage Radiographs", *Int. J. Radiation Oncology Biol. Phys.*, vol. 47, No. 3, (2000), 825-839.

Ragan, "Correction for Distortion in a Beam Outline Transfer Device in Radiotherapy CT-Based Simulation", *Med. Phys.* 20(1), (Jan./Feb. 1993), 179-185.

Redpath, et al., "Use Stimulator and Treatment Planning Computer as a CT Scanner for Radiotherapy Planning", Abstract, *Proceedings—Eighth International conference on the Use of Computers in Radiation Therapy* held in Toronto, Canada, IEEE, New York, NY, (1984), 281-187.

Reynolds, et al., "An Algorithm for Three-Dimensional Visualization of Radiation Therapy Beams", Abstract, *Med Phys*, vol. 15 (1), (Jan.-Feb. 1988), 24-28.

Rizo, et al., "Comparison of Two Three-Dimensional X-Ray Cone-Beam-Reconstruction Algorithms with Circular Source Trajectories", *J. Opt Soc. Am. A*, 10, (1991), 1639.

Ruchala, K J., et al., "Megavoltage CT Tomography System", *Phy. Med. Biol.*, vol. 44, (1999), 2597-2621.

Siewerdsen, et al., *Med. Phys. 26*, (1999), 2635-2647.

Siewerdsen, et al., *Med. Phys. 26*, (1999), 1624-1641.

Siewerdsen, J H., et al., "Cone-Beam Computed Tomography with a Flat-Panel Imager: Magnitude and Effect of X-Ray Scatter", *Med. Phys.*, vol. 28, No. 2, (Feb. 2001), 220-231.

Siewerdsen, J H., et al., "Optimization of X-Ray Imaging Geometry (With Specific Application to Flat-Paneled Cone-Beam Computed Tomography)", *Med. Phys.*, vol. 27, No. 8, (Aug. 2000), 1903-1914.

Swindell, W , et al., "Computed Tomography with a Linear Accelerator with Radiotherapy Applications", *Med. Phys.*, vol. 10, No. 4, (Jul./Aug. 1983), 416-420.

Uematsu, M , et al., "A Dual Computed Tomography Linear Accelerator Unit for Stereotactic Radiation Therapy: A New Approach Without Cranially Fixated Stereotactic Frames", *Int. J. Radiation Oncology Biol. Phys.*, vol. 35, No. 3, (1996), 587-592.

Uematsu, M , et al., "Daily Positioning Accuracy of Frameless Stereotactic Radiation Therapy with a Fusion of Computed Tomography and Linear Accelerator (FOCAL) Unit: Evaluation of Z-axis with a Z-marker", *Radiotherapy and Oncology*, vol. 50, No. 3, (Mar. 1999), 337-339.

Uematsu, M , et al., "Infractional Tumor Position Stability During Computed Tomography (CT)—Guided Frameless Seterotactic Radiation Therapy for Lung or Liver cancers with a Fusion of CT and Linear Accelerator (FOCAL) Unit", *Int. J. Radiation Oncology Biol. Phys*, vol. 48, No. 2, (2000), 443-448.

Varian, Search Report mailed Jan. 21, 2011; EP Appln No. 03786979.9.

Yan, et al., "Deriviation and Analysis of a Filtered Backprojection Algorithm for Cone Beam Projection", *IEEE Trans. Medical Imaging*, 10, (1991), 462.

Varian Medical Systems, Inc., Communication pursuant to Article 94(3) EPC, EP Application No. 03 786 979.9-1657, dated Jan. 30, 2014, 8 pages.

\* cited by examiner

Figure 1- Simulator kV Cone Beam CT Diagram

Figure 3- MV Cone Beam CT Diagram

MULTI-MODE CONE BEAM CT RADIOTHERAPY SIMULATOR AND TREATMENT MACHINE WITH A FLAT PANEL IMAGER

CROSS-REFERENCE TO RELATED APPLICATIONS

This application is a continuation of U.S. patent application Ser. No. 11/891,505. filed Aug. 10, 2007 issued on Feb. 14, 2012, as U.S. Pat No. 8,116,430, which is a continuation of U.S. patent application Ser. No. 10/324,227 filed Dec. 18, 2002 and issued as U.S. Pat. No. 7,945,021 on May 17, 2011.

TECHNICAL FIELD

The present invention pertains in general to therapeutic radiology. In particular, the invention involves imaging devices.

BACKGROUND

An objective of radiation therapy is to maximize the amount of radiation to a target volume (e.g., a cancerous tumor) and minimize the amount of radiation to healthy tissues and critical structures. The process of identifying the precise location of the target volume immediately prior to a dose of therapeutic radiation is key to the objective. Since each patient is treated over 30 to 40 fractionated sessions, then the time allowed for each session is relatively short, e.g. 10 to 15 minutes, so the process must be fast as well as accurate.

In the case of electronic portal imaging, megavolt therapeutic X-rays emerging from the patient can be used to generate images. However, this method of target location generates images of low contrast and quality, in addition to incidentally damaging healthy tissue. As a result, imaging with megavoltage (MV) radiation is used primarily for portal verification, that is, to confirm that the treatment volume is being radiated.

Radiotherapy simulator machines have been used to perform the pre-treatment analysis of the target volume before a radiotherapy treatment machine applies the therapeutic radiation. However, traditional radiotherapy simulator machines use bulky image intensifier tube detectors to capture images of the treatment volume. These image intensifier tube detectors have the disadvantage of being very large relative to their imaging area. They also have image spatial distortions from their spherical shaped input surface and the orientation of the intensifier tube with the Earth's magnetic field.

SUMMARY OF AN EMBODIMENT OF THE INVENTION

A multi-mode cone beam computed tomography radiotherapy simulator and treatment machine is disclosed. The radiotherapy simulator and treatment machine both include a rotatable gantry on which is positioned a cone-beam radiation source and a flat panel imager. The flat panel imager captures x-ray image data to generate cone-beam CT volumetric images used to generate a therapy patient position setup and a treatment plan.

BRIEF DESCRIPTION OF THE DRAWINGS

The present invention is illustrated by way of example and not limitation in the figures of the accompanying drawings, in which like references indicate similar elements and in which.

DETAILED DESCRIPTION

In the following description, for purposes of explanation, numerous specific details are set forth in order to provide a thorough understanding of the present invention. It will be evident, however, to one skilled in the art that the present invention may be practiced without these specific details. In some instances, well-known structures and devices are shown in gross form rather than in detail in order to avoid obscuring the present invention. These embodiments are described in sufficient detail to enable those skilled in the art to practice the invention, and it is to be understood that other embodiments may be utilized and that logical, mechanical, electrical, and other changes may be made without departing from the scope of the present invention.

A clinical therapy simulation machine having a cone-beam computed tomography (CT) radiation source and a flat-panel imager is described. The clinical therapy simulation machine is capable of manipulating the flat-panel imager and the cone beam CT radiation source to generate x-ray images for determining patient setup/alignment and a clinical treatment plan to be implemented by a clinical treatment machine.

Figure 1:
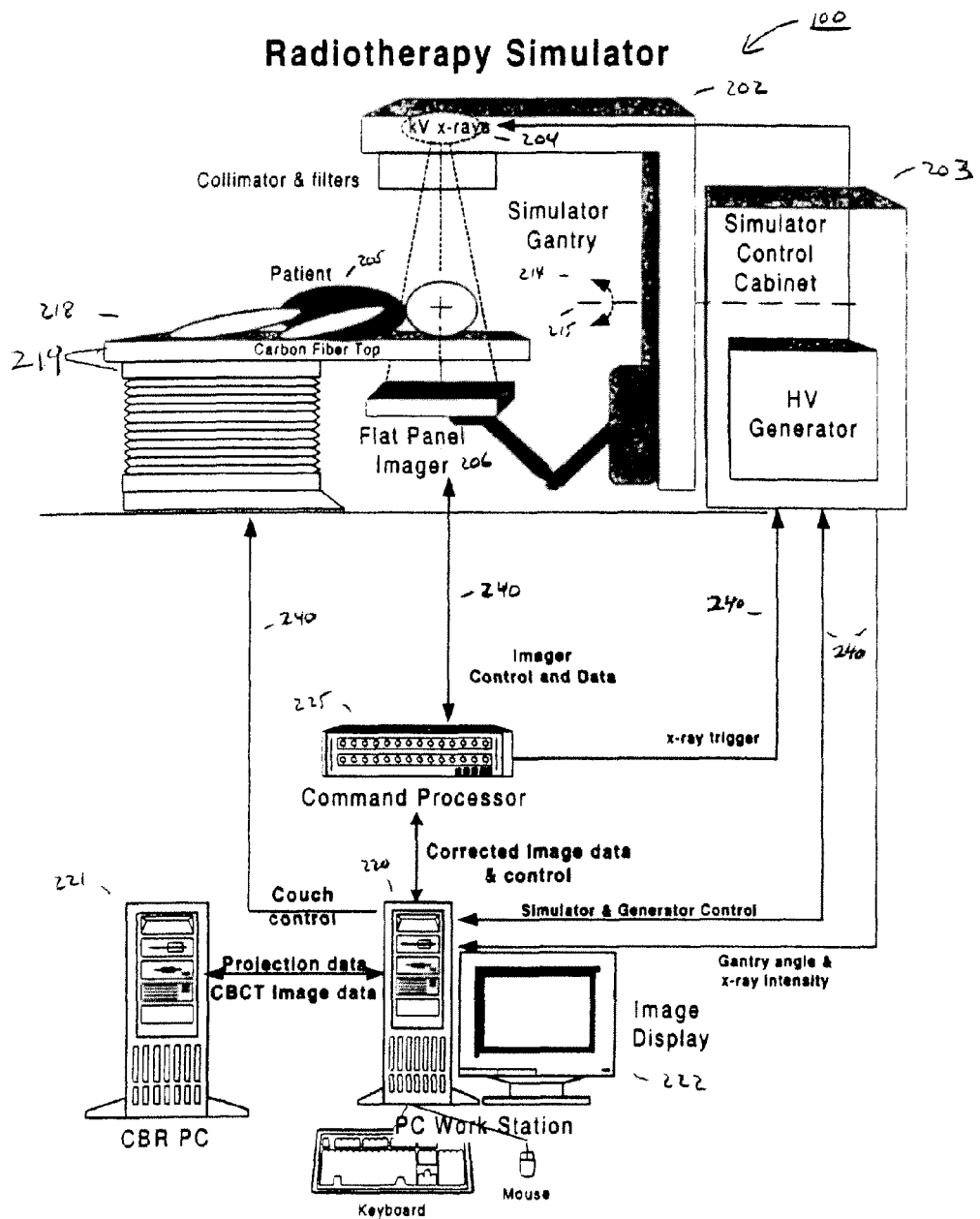
FIG. 1 is an illustration of a side view of one embodiment of a simulation treatment machine.

FIG. 1 is a side view of one embodiment of a simulation treatment machine 100. The simulation treatment machine 100 includes a rotatable gantry 202 pivotably attached to a drive stand 203. A cone-beam CT radiation source 204 and a flat panel imager 206 oppose each other and are coupled to the rotatable gantry 202. In one embodiment, the cone-beam CT radiation source is a kilovoltage radiation source generally in the 50 to 150 kilovolt (kV) energy range, and for example at 125 kilovolts peak (kVp).

A treatment couch 218 is positioned adjacent to the gantry 202 to place the patient and the target volume within the range of operation for the radiation source 204 and the imager 206. The couch 218 may be connected to the therapy simulator rotatable gantry via a communications network and is capable of translating in multiple planes plus angulation (e.g., see 219) for positioning and re-positioning the patient 205 and therefore the target volume.

The gantry 202 can rotate 214 about an isocenterline 215 to place the radiation source 204 and imager 206 at any position 360 degrees around the target volume, for example, to generate CT scan image data. As will be described, cone-beam CT image data can be used to generate a three-dimensional representation of the patient anatomy and the target volume. The image data may further be used to generate a treatment plan to tailor a dose of therapeutic radiation to the target volume.

Figure 2:
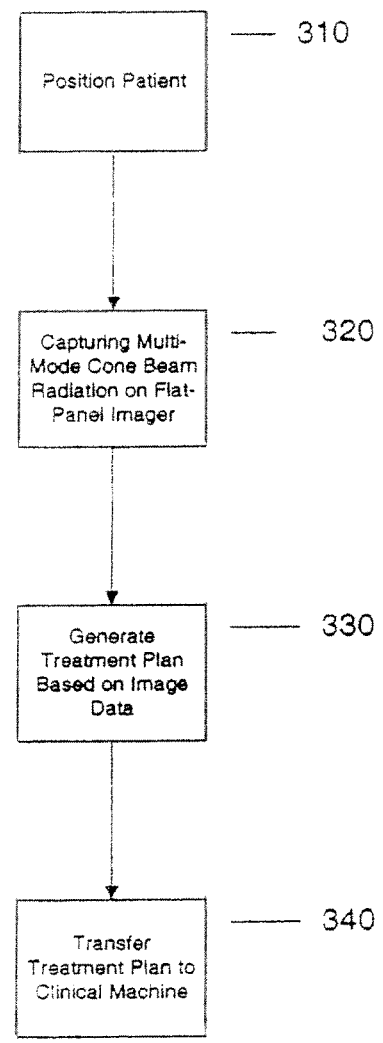
FIG. 2 is an illustration of a process flow of one embodiment of a method for generating a treatment plan.

FIG. 2 is a process diagram of one embodiment of a method for generating a treatment plan. At block 310, a patient 205 is placed on the treatment couch 218 and the couch 218 positioned relative to the simulation machine 100. At block 320, the gantry 202 rotates around the patient 205 while the radiation from the cone-beam CT radiation source 204 impinges the flat-panel imager 206. The gantry 202 rotates and collects image data until a computer can calculate a representation of the patient and the target volume. For example, software in a computer may take the image data to generate cone-beam CT volumetric image data for generation of a treatment plan. At block 330, a treatment plan may be generated from the collected image data. The treatment plan may then be transferred, at block 340, to a clinical treatment machine to provide instructions to the clinical treatment machine, for example, to position a therapeutic radiation source to apply a radiation dose to a target volume, and to minimize dose to health tissue and critical structures.

In one embodiment the flat panel imager 206 is a real-time digital x-ray imager incorporating a large-area amorphous silicon sensor array with a high-sensitivity cesium iodide (CsI) scintillator. The flat panel imager may include a receptor module that incorporates the amorphous silicon sensor array, which accepts incoming X-ray photons and converts them to a digital video signal. The X-ray to light conversion may be provided by a thin or thick columnar Csl:Tl (cesium iodide: thallium doped) scintillator The scintillator may be vacuum deposited in a thin (e.g. 0.6 mm) layer or include individual CsI crystals (e.g., being approximately 9 mm thick with an approximate 0.38 mm ×0.38 mm pixel pitch) supported in a housing with an aluminum window (e.g., approximately 1 mm thick). The top of the thin CsI scintillator may be coated with a reflective powder/epoxy mixture. Five sides of each thick crystal may be coated with a reflecting powder/epoxy mixture. The sixth side may be in contact with and face the flat-panel sensor. Alternatively, the scintillator components may have other dimensions.

The receptor module may also include a power supply module (e.g., 24 VDC power), interconnecting cables (e.g., fiber optic control and data cables), and drive and readout circuits followed by digital data conversion and transmission capabilities well known to those of ordinary skill in the art.

It should be appreciated that the flat panel imager may be a two-dimensional large flat panel imager that can operate, for example, at 15 to 30 frames per second (fps) over a wide range of dose. In this way, fluoroscopic, radiographic and cone-beam CT imaging can all be achieved with the same flat panel system. Typically, 300-900 projections may be collected during a single rotation of the gantry depending on the image resolution and dose requirements. Fewer projections allow for a faster collection of cone-beam CT image data (e.g., in 20 to 40 seconds depending on gantry speed limits), thereby, allowing for lower dose cone-beam CT images with less patient motion artifacts. Alternatively, the images may operate at other frame rates.

In one embodiment, the flat panel imager has a landscape orientation, an active area of 39.7×29.8 cm$^2$ with 194 micron pixel pitch, and a pixel count of 2048×1536 pixels. It can operate at a frame rate of 7.5 fps in full resolution mode and at a frame rate of 30 fps in 2×2 binned mode—where the pixel count is reduced to 1024×768 pixels$^2$ For example, the flat panel imager may be an amorphous silicon (a-Si) imager available from Varian Medical Systems of Palo Alto, Calif., under the tradename PaxScan™ 4030A. The PaxScan™ 4030A detectors are each 40 cm×30 cm. The detectors may be coupled to signal processing circuitry comprising a preamplifier stage with dynamically controllable signal gain, as described in U.S. Pat. No. 6,486,808, filed on Oct. 16, 2001, assigned to the assignee of the present invention and incorporated by reference, herein, to improve contrast resolution and dynamic range.

The readout electronics may also be located out of the path of the primary cone-beam CT radiation source 204. The flat panel imager 206 may also employ a split data-line where the top half of the array and the bottom half of the array are read out simultaneously. This allows the imager 206 to read out more rapidly and reduces the parasitic capacitance of the data-lines, which in turn reduces the noise gain of the readout charge amplifiers. It should be appreciated that only half of the frame time is used to read out the pixels. During the rest of the frame time, the sensor can be irradiated without generating any interference patterns due to the pulsing of the cone-beam CT radiation source 204. In addition, it should also be appreciated the control system of the flat panel imager 206 allows an external synchronization signal (from the computer 220) to initiate the readout of a frame. This allows the user to externally control when the imager will acquire an image.

In one embodiment, a command processor module 225 manages the receptor module, processes the digital video, and provides interfaces to other components of the simulator 100. The command processor module 225 may include a microcontroller-based, single board computer running a real-time operating system with acquisition, control, and interface software. Also, included in the command processor may be a high-speed digital video interface card, a dedicated image processor card to perform real-time image corrections, a system interface card, and a parallel output to transmit image data to an external image processor and display. Scan-converted digital and analog video may also be provided.

The captured cone-beam CT image projection data may be delivered and stored to a computer 220. As shown in FIG. 1, the computer 220 connects to the simulator 100 and the command processor 225 via communications network 240. The computer 220 may control the synchronized movement of the simulator 100 including the rotatable gantry 202, the cone-beam CT radiation source 204, imager 206, and the treatment couch 218. Specifically, the computer 220 may be used by an oncologist to display image projection data on a monitor 222, control the intensity of the cone-beam CT radiation source 204, and control the gantry angle.

The cone-beam CT image projection data may also be transferred to a cone-beam CT reconstruction computer 221 that includes software designed to achieve rapid cone-beam CT image generation. The computer 221 can merge or reconstruct the image data into a three-dimensional representation of the patient and target volume. In one embodiment, cone-beam CT reconstruction software may allow for full-cone and partial-cone input data that can produce cone-beam CT images (e.g., approximately 26 to 48 cm diameter) at a specific source-to-imager distance (e.g., 140-150 cm). In addition, in this way, the clinical simulator machine 100 and cone-beam CT reconstruction software may also allow for large diameter (e.g., approximately 48 cm) axial image volumes.

In one embodiment, the cone-beam CT reconstruction software may transform the image projection data into volumetric CT image data. The volumetric CT image data may include full-fan and/or partial cone image data to reconstruct head size (e.g. 26 cm diameter×17 cm length) and body size (e.g. 48 cm diameter×15 cm length) volumes. For example, the partial-cone method may be used to obtain body size scans when the flat panel imager is not long enough to image the full body in each projection. If the 15 or 17 cm axial section is not wide enough and therefore does not cover sufficient anatomical volume, then multiple scans can be performed. For example, in the two scan case, the patient may be moved axially by 15 or 17 cm couch movements between scans and the reconstructed image volumes may then be merged to provide a 30 to 34 cm axial view.

In one embodiment, prior to reconstruction, the image projection data is preprocessed to account for x-ray beam and detector properties and the system electronic and geometric properties. The algorithm and its implementation is similar to that used in single slice computer tomography in reconstruction of fan beam data obtained with a one-dimensional detector. For partial cone beam reconstruction, the partial cone image projection data is extended to full cone beam image data and then reconstructed using a full cone beam reconstruction algorithm well known to those of ordinarily skill in the art, such as, for example, the Feldkamp cone beam reconstruction technique. It should be understood that the extension of the partial cone beam image data is performed using techniques similar to those used for the extension of partial fan data in well known single slice fan beam computer tomography.

In one embodiment, using the shape and distance data determined from the generated dimensional representation, the target volume may be automatically identified by the computer system 221 and/or by the inspection of an oncologist. The identified target volume may be applied to a radiotherapy planning computer system 220, which creates a treatment plan to be implemented by a clinical treatment machine. The visualization of the data along arbitrary planes, e.g. sagital, coronal, axial, beams eye view, etc., can be displayed to assist the oncologist. To further enhance the visualization, averaging of volume image data perpendicular to the plane of view, i.e. rectangular voxels may be used.

Figure 3:
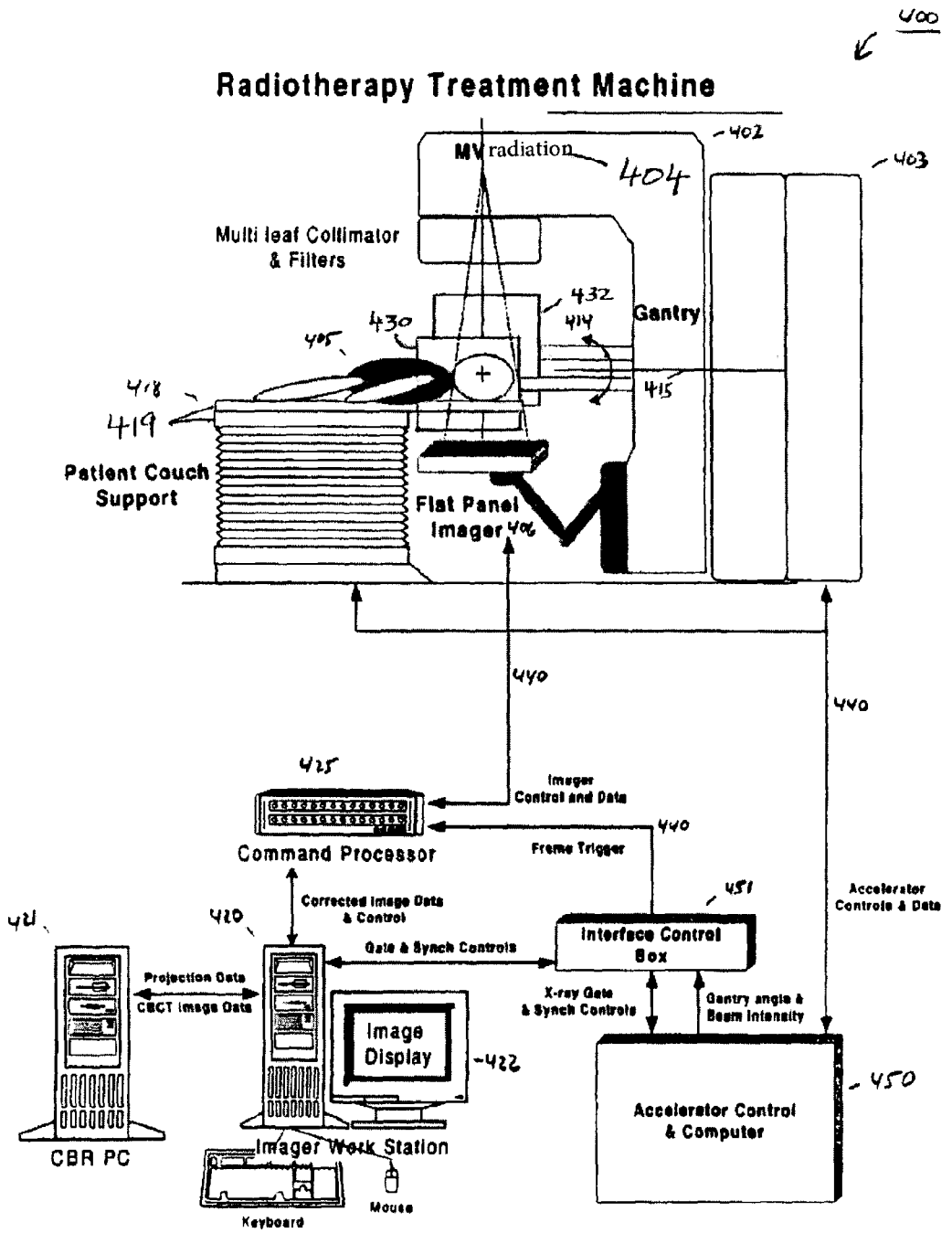
FIG. 3 is a side view of one embodiment of a clinical treatment machine.

FIG. 3 is a side view of one embodiment of a clinical treatment machine 400 that may implement the treatment plan generated by the simulator 100 and treatment planning computer 220. The clinical treatment machine 400 includes a rotatable gantry 402 pivotably attached to a drive stand 403. A cone-beam CT radiation source 404 and a flat panel imager 406 oppose each other and are coupled to the rotatable gantry 402. In one embodiment, the cone-beam CT radiation source 404 is a megavoltage (MV) radiation source generally in the 4 to 25 MV energy range, for example, at 6 MV.

A treatment couch 418 is positioned adjacent to the gantry 402 to place the patient 405 and the target volume within the range of operation for the radiation source 404 and the imager 406. The couch 418 can be capable of translating in multiple planes plus angulation (e.g., see 419) for positioning and re-positioning the patient 405 and therefore the target volume.

The gantry 402 can rotate 414 about an isocenterline 415 to place the cone-beam CT radiation source 404 and imager 406 at any position 360 degrees around the target volume. The resulting megavoltage cone-beam CT image data can then be used to tailor a dose of therapeutic radiation based on at least the generated pre-defined treatment plan.

Figure 4:
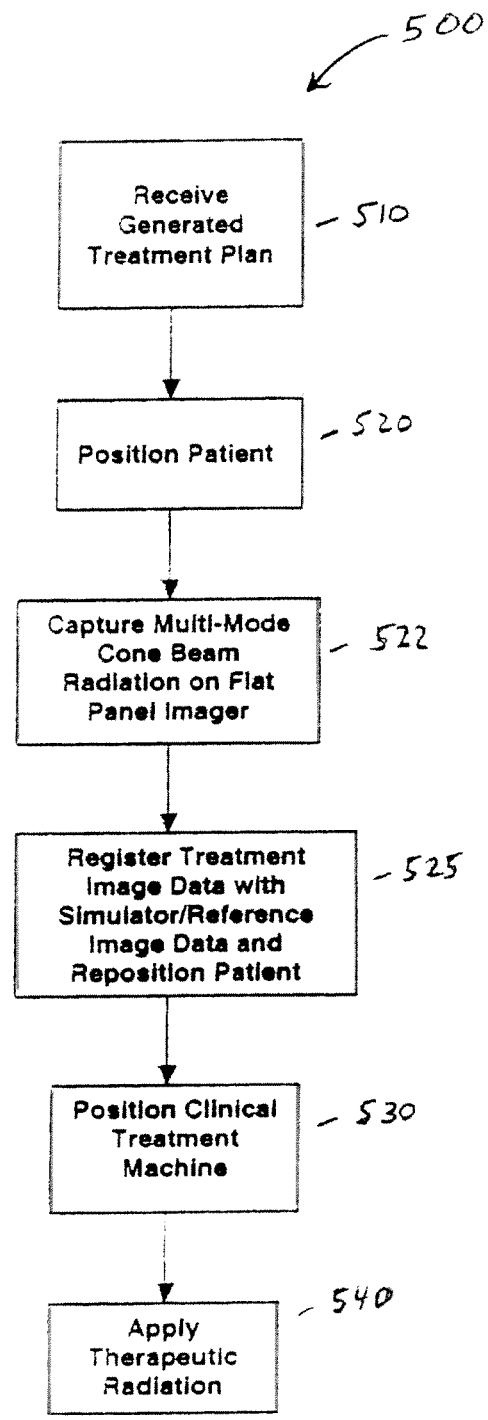
FIG. 4 illustrates a process flow of one embodiment of a method for implementing a treatment plan.

FIG. 4 is a process diagram of one embodiment of a method for implementing a treatment plan. At block 510, an accelerator control computer 450 is provided with the treatment plan generated from the clinical simulator machine 100 for a specific patient. For example, the treatment plan may provide initial targeting information about the target volume. At block 520, a patient 405 is placed on the treatment couch 418 and the couch 418 is positioned relative to the clinical treatment machine 400. At block 522, multi-mode cone beam radiation from the radiation source 404 is captured by the imager 406 to generate images of the target volume. At block 525, the captured image data can be compared/registered with the simulator or other reference images to determine the patient repositioning required, if any, before treatment. Image data can also be taken without repositioning to determine the random and systematic errors in treatment position, if any. At block 530, the gantry 402 is rotated around the patient 405 to a treatment position based on the generated treatment plan. At block 540, a therapeutic radiation dose is applied to the target volume from the cone-beam CT radiation source 404 based on the generated treatment plan. The cone-beam CT radiation source 404 also impinges the flat-panel imager 406 with radiation. In this way, the flat panel imager 406 may provide verification that the target volume is properly targeted. The process 500 may be repeated until the treatment session is complete.

The flat panel imager 406 is similar to the flat panel imager 206 including the corresponding interconnects with a command processor module 425, a computer 420, a monitor 422, and a cone-beam reconstruction computer 421, corresponding with the command processor module 225, the computer 220, a monitor 422, and the cone-beam reconstruction computer 221, as described above. However, in one embodiment, the flat panel imager 406 may have its electronics unfolded from beneath the imager 406 and the input screen coating may be thicker (e.g., 9 mm vs. 0.6 mm). An example of a flat panel imager that may be used in the present invention is described in U.S. Pat. Ser. No. 10/013,199, now U.S. Pat. Ser. No. 6,800,858 B1, filed on Nov. 2, 2001, assigned to the assignee of the present invention and incorporated herein by reference.

The imager 406 may also interface with an accelerator interface control box 451. The accelerator interface control box 451 interfaces with an accelerator control computer 450 to provide synchronization and gated control between the imager 406 and the cone-beam CT radiation source 404 during treatment based on the generated treatment plan. As shown in FIG. 3, interface control box 451, command processor module 425, and accelerator control computer 450 connect to simulator 400 via communications network 440. This allows single or multiple beam pulse images that are not affected by accelerator noise during readout.

In one embodiment, the accelerator interface control box 451 includes a timing interface. The timing interface coordinates acquisition by the flat panel imager 406 and pulsing of the cone-beam CT radiation source 404. With this interface, as little as one radiation pulse (0.028 cGy at the isocenter) can be used to form projection images.

In one embodiment, the timing interface includes a National Instruments PCI 6602 data acquisition card from National Instruments Corporation of Austin, Tex. USA, that contains hardware and firmware for counting and timing pulses; computer software that provides control logic; and a user interface for the interface system. Alternatively, other cards may also be used.

A master clock signal is derived from a sync signal of the cone-beam CT radiation source 404, which may operate at 360 pulses/s (6 MV) or 180 pulses/s (15-18 MV), according to one embodiment. Using a counter on the National Instruments PCI 6602 card, the sync signal is divided down to produce a master clock signal, and hence are timed relative to the production of cone-beam CT radiation pulses from the cone-beam CT radiation source 404.

The master clock signal may be used to generate two control pulses, one that gates the cone-beam CT radiation source 404 on and off and the other that triggers the flat panel imager 406. In one embodiment, the frequency of these pulses is user selectable, and may be any value below 30 pulses/sec. The relative timing of the two pulses may also be user selectable. When the flat panel imager 406 is triggered there is a period, while the image is being read out (half a frame time) during which no beam from the cone-beam CT radiation source 404 is desired. A user can enter the appropriate delay that will prevent irradiation during the frame readout period of the imager. The length of the gate pulse of the cone-beam CT radiation source 404 is also user selectable. By adjusting the width of the gate pulse, the user can control the number of beam pulses emitted by the cone-beam CT radiation source 404 during each gate pulse.

It should be appreciated that the MV cone-beam CT flat panel imager 406 has a high quantum efficient 9 mm thick CsI:Tl screen (e.g., approximately 10% efficient at 6 MV), which preserves spatial resolution and minimizes dose to the patient by at least a factor of 5 over a standard 1 mm thin copper plate and less than 1 mm GOS (gadolinium oxysulfide) screens used in standard flat panel and screen-camera portal imaging. Therefore, images with as low as one 6 MV accelerator beam pulse (e.g., 0.028 cGy) per frame may be collected. In addition, a low patient dose of 8 to 16 cGy per cone-beam CT data set may be yielded for 300 to 600 CT image frames or projections per data set. The lower dose of the MV cone-beam CT radiation allows for more frequent use on each patient during the typical 30 to 37 fractionated treatment sessions. Moreover, reduced spatial resolution on the MV cone-beam CT scans can be afforded for faster processing time using the cone-beam reconstruction software on the CBR computer 421 to achieve rapid image generation.

It should be appreciated that a separate kV cone-beam CT radiation source (optional and shown as source 430) and another opposing flat panel imager (as described above on the simulator optional and shown as imager 432) may also be coupled to the gantry 402 to perform a diagnostic cone-beam CT scan. For example, the kV cone-beam CT radiation source and opposing flat panel imager may be coupled to the treatment machine gantry 402 at an off axis of e.g. forty-five or ninety degrees from the MV cone-beam radiation source 404 and opposing imager 406. As before, software in the computers 420 and/or 421 may generate the three-dimensional representation of the patient anatomy and target volume from the cone-beam CT image data provided by the kV radiation source. The clinical treatment machine 400 may use the kV cone-beam CT image data to make any necessary adjustments to the treatment plan based on identified movement of the target volume or to determine the amount of patient repositioning required by the treatment couch 418 or collimator movements. In this way, the kV cone-beam CT radiation source and flat panel imager share a common axis of rotation with the MV cone-beam CT radiation source 404 and provide additional information for aligning the patient to the generated simulation treatment plan.

It should also be appreciated that in this way, either the clinical simulator machine 100 and/or the clinical treatment machine 400 diagnostic cone-beam CT image data can be used as a reference for applying the MV radiation beams.

It should also be understood that it is not necessary for the therapeutic radiation to be applied from the exact position(s) where any of the previously generated CT images were taken since the computer software can provide virtual two-dimensional representations for any desired radial location in-between the images.

It should be understood that although the clinical treatment machine 400 has been described as having a cone-beam radiation source, in alternative embodiments beam shaping, along with intensity modulation, may also be implemented based on the generated treatment plan by directing a therapeutic beam through a dynamic multileaf collimator. The multileaf collimator may include a series of stacked metal shims having a center of shim pairs where each shim of the pairs may be individually moved to create a shaped opening capable of shaping the therapeutic beam. To be effective, the radiation field should be large enough to radiate the entire tumor while at the same time minimize radiating healthy tissue. The collimator may be dynamic in that the shims can rapidly move to reshape the beam, which results in blocking the therapeutic beam from striking certain areas of the target volume based on the treatment plan. Such dynamic shaping may result in different areas of the tumor receiving different amounts of radiation over the time that a radiation dose is applied.

It should be appreciated that more or fewer processes may be incorporated into the methods illustrated in FIGS. 2 and 4 without departing from the scope of the invention and that no particular order is implied by the arrangement of blocks shown and described herein. It further will be appreciated that the method described in conjunction with FIGS. 2 and 4 may be embodied in machine-executable instructions (e.g. software). The instructions can be used to cause a general-purpose or special-purpose processor that is programmed with the instructions to perform the operations described. Alternatively, the operations might be performed by specific hardware components that contain hardwired logic for performing the operations, or by any combination of programmed computer components and custom hardware components. The methods may be provided as a computer program product that may include a machine-readable medium having stored thereon instructions that may be used to program a computer (or other electronic devices) to perform the methods. For the purposes of this specification, the terms "machine-readable medium" shall be taken to include any medium that is capable of storing or encoding a sequence of instructions for execution by the machine and that cause the machine to perform any one of the methodologies of the present invention. The term "machine-readable medium" shall accordingly be taken to included, but not be limited to, solid-state memories, optical and magnetic disks, and carrier wave signals. Furthermore, it is common in the art to speak of software, in one form or another (e.g., program, procedure, process, application, module, logic . . . ), as taking an action or causing a result. Such expressions are merely a shorthand way of saying that execution of the software by a computer causes the processor of the computer to perform an action or produce a result.

It should be appreciated that a clinical simulation machine having a cone-beam radiation source and flat-panel imagers, as described, allows for identification of a target volume via fluoroscopic, radiographic, and cone-beam CT imaging. In this way, the generation of the treatment plan via the clinical simulation machine prior to the application of therapeutic radiation, increases the accuracy of treating the tumor target. Furthermore, embodiments of the invention as described above may capture images while the gantry is continuously rotating versus traditional systems that stop and shoot every, approximately, four degrees around the patient, thereby further lessening the time for completion.

It should also be appreciated that the cone-beam volumetric reconstruction software can utilize image projection data at non-uniformly spaced gantry angles. Thus the data collection does not require a precise gantry speed of rotation. There is a normalizing detector at the radiation source, which is used to correct for system output variations. In one embodiment, the support arms for the images 206 and 406 are sufficiently precise in mechanical stability during gantry rotation that no compensating spatial corrections are required.

Although the present invention has been described with reference to specific exemplary embodiments, it will be evident that various modifications and changes may be made to these embodiments without departing from the broader scope of the invention as set forth in the claims. Accordingly, the specification and drawings are to be regarded in an illustrative rather than a restrictive sense.

What is claimed is:
1. A radiation treatment system, comprising:
   a rotatable gantry;
   a treatment source;

a cone-beam radiation source coupled to the rotatable gantry;

a flat-panel imager coupled to the rotatable gantry, wherein the flat-panel imager is operable to capture image projection data of a patient;

a first logic that reconstructs a cone-beam computer tomography (CT) volumetric image data based on the image projection data;

a patient support to support the patient; and a second logic configured to control the patient support and place the patient in an operative position to begin a treatment based on the cone-beam CT volumetric image data or the image projection data.

2. The radiation treatment system of claim 1, wherein the first logic and the second logic comprise at least one of hardwired logic and a programmable computer component and wherein the programmable computer component comprises a processor.

3. The radiation treatment system of claim 1, wherein the flat-panel imager includes an amorphous silicon sensor array and includes a cesium iodide scintillator, wherein the cesium iodide scintillator includes a mixture in a large matrix of cesium iodide crystals coated with a reflective powder and epoxy.

4. The radiation treatment system of claim 1, wherein the flat-panel imager is capable of fluoroscopic imaging, radiographic imaging, and cone-beam CT imaging.

5. The radiation treatment system of claim 1, wherein the flat-panel imager is capable of generating image projection data at 15 to 30 frames per second.

6. The radiation treatment system of claim 1, further comprising:

a computing unit, coupled to the rotatable gantry, to store the image projection data captured by the flat-panel imager.

7. The radiation treatment system of claim 1, wherein the treatment source is a megavoltage radiation source.

8. The radiation treatment system of claim 1, wherein controlling the patient support and placing the patient in the operative position to begin the treatment comprises:

positioning the patient on the patient support; then controlling the patient support to re-position the patient so that a center of the treatment source is matched with a center of a treatment plan.

9. The radiation treatment system of claim 8, wherein positioning the patient on the patient support comprises placing the patient on the patient support, and then positioning the patient support to place a target volume of the patient within the range of operation (1) of the treatment source and (2) of the flat-panel imager; and wherein controlling the patient support to re-position the patient comprises controlling the patient support to re-position the target volume based on comparing (1) the cone-beam CT volumetric image data or the image projection data showing the center of the treatment source with (2) reference images of the treatment plan showing the center of the treatment plan.

10. A method to prepare for a clinical treatment, comprising:

obtaining image projection data from transmitting at least a portion of a cone-beam from a radiation source through a target volume onto a flat panel imager;

generating cone-beam computer tomography (CT) volumetric image data based on the obtained image projection data; and placing a patient in an operative position to begin the clinical treatment based on the cone-beam CT volumetric image data or the image projection data.

11. The method of claim 10, further comprising:

emitting the cone-beam from the radiation source, wherein the radiation source is part of a clinical treatment machine; and transmitting at least a portion of the cone-beam through the target volume, wherein the clinical treatment machine has a rotatable gantry pivotably coupled at a pivot point to a frame.

12. The method of claim 10, wherein the radiation source is a cone-beam computed tomography radiation source, and wherein the image projection data is generated from the flat-panel imager capturing radiation from the cone-beam computed tomography radiation source passing through the target volume.

13. The method of claim 10, wherein obtaining comprises capturing the image projection data at a frame rate in the range of 15-30 frames per second.

14. The method of claim 10, further comprising radiating the target volume with a megavoltage radiation source.

15. A method of claim 10, wherein placing the patient in the operative position comprises:

determining a patient position relative to a high-energy radiation treatment beam of a treatment radiation source of a clinical treatment machine using logic comprising at least one of hardwired logic and a programmable computer component.

16. The method of claim 15, further comprising:

emitting the cone-beam from the radiation source, wherein the radiation source is part of the clinical treatment machine; and transmitting at least a portion of the cone-beam through the target volume, wherein the clinical treatment machine has a rotatable gantry pivotably coupled at a pivot point to a frame.

17. The method of claim 15, wherein the radiation source is a cone-beam computed tomography radiation source, and wherein the image projection data is generated from the flat-panel imager capturing radiation from the cone-beam computed tomography radiation source passing through a target volume.

18. The method of claim 15, wherein obtaining comprises capturing the image projection data at a frame rate in the range of 15-30 frames per second.

19. The method of claim 15, further comprising:

generating a treatment plan for the clinical treatment machine based on the cone-beam CT volumetric image data; and using the treatment plan to instruct the clinical treatment machine to at least adjust a treatment radiation source into position to align a treatment volume with the treatment radiation source, wherein the radiation source is a kilovoltage radiation source and wherein the treatment radiation source comprises a megavoltage radiation source to radiate the treatment volume with radiation.

20. The method of claim 10, wherein placing the patient in the operative position comprises:

positioning the patient on a patient support; then controlling the patient support to re-position the patient so that a center of a treatment radiation source is matched with a center of a treatment plan.

21. The method of claim 20, wherein positioning the patient on the patient support comprises placing the patient on the patient support, and then positioning the patient support to place a target volume of the patient within the range of operation (1) of the treatment source and (2) of the flat-panel imager; and wherein controlling the patient support to re-position the patient comprises controlling the patient support to re-position the target volume based on comparing (1) the cone-beam CT volumetric image data or the image projection data showing the center of the treatment radiation source with (2) reference images of the treatment plan showing the center of the treatment plan.

* * * * *